United States Patent
Bortolo et al.

(10) Patent No.: US 10,961,497 B2
(45) Date of Patent: Mar. 30, 2021

(54) METHOD FOR CONCENTRATING A CELL SUSPENSION COMPRISING A MUCILAGINOUS BIOMASS OF OLEAGINOUS YEASTS

(71) Applicant: ENI S.p.A., Rome (IT)

(72) Inventors: Rossella Bortolo, Novara (IT); Daniele Bianchi, Arese (IT); Mario Baldassarre, Novara (IT)

(73) Assignee: ENI S.p.A., Rome (IT)

( * ) Notice: Subject to any disclaimer, the term of this patent is extended or adjusted under 35 U.S.C. 154(b) by 0 days.

(21) Appl. No.: 15/749,824

(22) PCT Filed: Aug. 5, 2016

(86) PCT No.: PCT/IB2016/054734
§ 371 (c)(1),
(2) Date: Feb. 2, 2018

(87) PCT Pub. No.: WO2017/021931
PCT Pub. Date: Feb. 9, 2017

(65) Prior Publication Data
US 2018/0223248 A1    Aug. 9, 2018

(30) Foreign Application Priority Data
Aug. 6, 2015  (IT) .................. 102015000042925

(51) Int. Cl.
| | |
|---|---|
| *C12N 1/16* | (2006.01) |
| *C12N 1/02* | (2006.01) |
| *C12N 1/00* | (2006.01) |
| C12P 19/00 | (2006.01) |

(52) U.S. Cl.
CPC ............... *C12N 1/16* (2013.01); *C12N 1/005* (2013.01); *C12N 1/02* (2013.01); *C12N 2500/34* (2013.01); *C12P 19/00* (2013.01); *Y02E 50/10* (2013.01)

(58) Field of Classification Search
CPC ........................................................ C12N 1/02
See application file for complete search history.

(56) References Cited

U.S. PATENT DOCUMENTS

2013/0289289 A1   10/2013   Franzosi et al.
2014/0004579 A1   1/2014    Sellers et al.

FOREIGN PATENT DOCUMENTS

WO    WO 2010/069516 A2   6/2010
WO    WO 2012/052368 A1   4/2012

OTHER PUBLICATIONS

Christophe et al. Appl Biochem Biotechnol 2012, 167:1270-1279.*
Huang et al. Bioresource Technology, 2009, 100:4535-4538.*
Schulze, 2014, Dr. Thesis, pp. 1-102.*
International Search Report and Written Opinion dated Nov. 14, 2016 in PCT/IB2016/054734, 13 pages.
Isabel Espinosa-Gonzalez, et al. "Hydrothermal treatment of oleaginous yeast for the recovery of free fatty acids for use in advanced biofuel production", Journal of Biotechnology, vol. 187, XP029075102, 2014 pp. 10-15.
Irnayuli R. Sitepu, et al. "Oleaginous yeasts for biodiesel: Current and future rends in biology and production", Biotechnology Advances, vol. 32, No. 7, XP055251520, 2014, pp. 1336-1360.

* cited by examiner

*Primary Examiner* — Bin Shen
(74) *Attorney, Agent, or Firm* — Oblon, McClelland, Maier & Neustadt, L.L.P.

(57) ABSTRACT

A method for concentrating, in order to favour the subsequent extraction process of intracellular lipids, a cell suspension containing a biomass of oleaginous yeasts fermented in fermentation broth under conditions that allow the intracellular accumulation of lipids, where the biomass contains significant quantities of mucilaginous material. The method includes:
  a) cultivating the oleaginous yeasts in a fermentation broth to obtain a cell suspension containing the mucilaginous biomass;
  b) subjecting the cell suspension obtained from a) to heat treatment, at a temperature between 95° C. and 120° C. and to acid treatment, to obtain a treated cell suspension containing the mucilaginous biomass containing intact oleaginous yeast cells; and
  c) concentrating the treated cell suspension obtained from b), by removing at least part of the fermentation broth to obtain a concentrated cell suspension.

13 Claims, No Drawings

METHOD FOR CONCENTRATING A CELL SUSPENSION COMPRISING A MUCILAGINOUS BIOMASS OF OLEAGINOUS YEASTS

This application is a 371 national stage application of PCT/IB2016/054734, filed Aug. 5, 2018, which claims priority to application Italy 102015000042925, filed Aug. 6, 2015.

The present invention falls within the field of biotechnologies and relates to a method for concentrating a cell suspension comprising a mucilaginous biomass of oleaginous yeasts.

More specifically, the present invention relates to a method for concentrating, in order to make easier the subsequent extraction process of intracellular lipids, a cell suspension comprising a biomass of oleaginous yeasts fermented in fermentation broth under conditions that allow the intracellular accumulation of lipids, said biomass being characterized in that it contains significant quantities of mucilaginous material.

Lipids produced microbiologically can be conveniently used for the production of bioplastics or as synthesis intermediates, particularly in the so-called "green-chemistry" field, or in the production of biofuels such as, for example, "biodiesel" or "green diesel", that can be used as such, or mixed with other fuels for motor vehicles.

For these types of applications, the microbiological production of lipids is proposed as an advantageous alternative to current production methods from renewable sources. With respect to the use of vegetable oils, microbiological processes are independent of climatic or geographical factors and do not compete with agricultural exploitation of the soil for food use. Another advantage lies in the fact that these processes exploit the property of microorganisms of reproducing rapidly by using inexpensive substrates, such as for example derivatives of the hydrolysis of lignocellulosic materials.

In the field of the microbiological production of lipids, oleaginous yeasts are particularly promising, i.e. yeasts that under specific cultivation conditions are able to accumulate lipids in quantities equal to or higher than 25% of their dry weight.

The use of oleaginous yeasts for the production of lipids is part of the known art.

International patent application WO2012/052368, for example, describes a process for the production of lipids from oleaginous yeasts selected from the genera *Rhodotorula, Lypomyces, Trigonopsis, Candida, Torulopsis* and *Pichia*, through fermentation processes in the presence of diluted sugary substrates, obtained from the hydrolysis of lignocellulosic biomasses including at least one polysaccharide. This process comprises: subjecting said biomass including at least one polysaccharide to acid hydrolysis obtaining a first mixture comprising a first solid phase and a first aqueous phase; feeding said first aqueous phase to a fermentation device in the presence of at least one oleaginous yeast obtaining a first fermentation broth comprising a first oleaginous cellular biomass; subjecting said first solid phase to acid hydrolysis or enzymatic hydrolysis obtaining a second mixture comprising a second solid phase and a second aqueous phase; feeding said second aqueous phase to said fermentation device in the presence of said first fermentation broth obtaining a second fermentation broth comprising a second oleaginous cellular biomass including lipids; subjecting at least a part of said second fermentation broth to microfiltration obtaining a retentate and a permeate; feeding said retentate to said fermentation device.

The lipids thus obtained can be advantageously used in the production of biodiesel or green diesel that can be used as such, or mixed with other fuels for motor vehicles.

The use of lipids of a microbiological origin, however, both in the preparation of biofuels such as, for example, biodiesel or green diesel, and also as synthesis intermediates, particularly in the so-called "green chemistry" field, competes with the use of fuels and chemical intermediates of a fossil origin, which are obtained through processes that are almost always more convenient economically. The study of processes capable of reducing the production costs of lipids of a biological, and particularly microbiological origin, and also improving their yield, is consequently still of great interest.

One of the greatest critical aspects relating to the microbiological production of lipids lies in the fact that the volumetric productivity (i.e. the quantity of lipids that can be obtained per volume unit of fermentation medium) is limited, and generally less than 100 g/L. The industrial application of these production processes therefore implies considerable fermentation volumes of said oleaginous microorganisms. These large volumes of cell suspension must naturally be treated to recover the resulting biomass and proceed with the extraction of the lipids, in large-sized plants, with high set-up and process costs.

The extraction methods of the lipids from the oleaginous microorganisms are also a part of the known art.

International patent application WO2012/078852, for example, describes a process for extracting triglycerides from microalgae by heat treatment of the cellular biomass in an acid environment and in the presence of a polar solvent, in order to "condition" the cell wall of the microalgae and favour the subsequent extraction with apolar solvent.

Almost all of the processes for extracting the lipid content from biomasses of oleaginous microorganisms envisage a preliminary step for recovering said biomasses from the culture mediums, at the end of the fermentation process, which is effected with physical means such as, for example, filtration, flocculation or centrifugation.

There are of course some exceptions: one of these, for example, is represented by patent application WO2001/053512, in which an extraction process of lipids from microorganisms is described, wherein said extraction can be effected directly in the culture medium in a fermenter after subjecting the biomass to lysis.

Generally however, as already mentioned, extraction processes of lipids from oleaginous microorganisms include a preliminary recovery step of the cellular biomass from the culture medium.

For example, international patent application WO2012/052368 envisages that the biomass, composed of oleaginous yeast cells, be recovered after fermentation by means of tangential microfiltration.

Analogously, Italian patent application MI2014A000761 describes a process for the production of lipids from oleaginous biomass by means of fermentation, after which said biomass comprising lipids is recovered from the culture medium by means of centrifugation.

In US2001/0046691 on the other hand, the oleaginous biomass is completely dehydrated, transferring the cell suspension coming from the fermenter to a heated drum dryer and thus causing the evaporation of the water contained in said suspension.

It should be pointed out, however, that some oleaginous yeasts, such as, for example, yeasts of the genera *Rhodoto-*

*rula, Rhodosporidium, Cryptococcus, Candida, Trichosporon*, and others, can produce bioemulsifiers and biosurfactants (as described, for example, by R. Shepherd, J. Rockey, I. W. Sutherland and S. Roller in "Novel bioemulsifier from microorganisms for use in foods" (1995), *J. Biotechnol.*, vol. 40 pages 207-217) which give the liquid cultures of said microorganisms a characteristic mucilaginous nature. In particular, the production of these mucilaginous substances occurs when high concentrations of biomass are reached during fermentations on an industrial scale.

It has often been observed that the surfactant properties of these substances make it difficult to recover the microorganisms that produce them from the culture medium.

Some studies (for example in K. Pavlova, L. Koleva, M. Kratchanova, I. Panchev "Production and characterization of an exopolysaccharide by yeast" (2004), *World J. of Microbiol. & Biotechnol.*, vol. 20, pages 435-439 and in I. N. A. Van Bogaert, J. Zhang, W. Soetaert "Microbial synthesis of sophorolipids" (2011) *Process Biochemistry*, vol. 46, pages 821-833) have shown that the biosynthesis of these mucilaginous substances on the part of oleaginous microorganisms can be stimulated by the same culture conditions used for favouring the accumulation of lipids. This means that it is often possible to demonstrate the existence of a correlation between the accumulation of lipids and the production of mucilaginous substances, to the extent that the microorganisms that produce more lipids are also those that, due to the formation of these substances, are more difficult to recover from the culture medium.

In these cases, in fact, the cell mass can acquire a density apparently equal to that of the culture medium, thereby preventing the separation of the liquid and solid phases by means of techniques, such as, for example, sedimentation or centrifugation, which exploit the difference in density between the phases to be separated.

Apparently, the production of mucilaginous substances on the part of mutant microorganisms hyperproducers of lipids causes the formation of stable emulsions that make it impossible to recover the microbial cells from the fermentation broth using techniques known in the art. An example of oleaginous yeast that produces mucilaginous substances is the oleaginous yeast mutant *Rhodosporidium azoricum* DSM 29495, described in patent application MI2014A002292.

In other cases, the production of mucilaginous material can be accompanied by a significant increase in the viscosity of the fermentation broth in the fermenter, as can be observed for example for some high-productivity cultures (having a concentration of biomass equal to or higher than 80 g of biomass per litre of culture) of yeasts of the species *Cryptococcus* or *Thrichosporon*, that can cause difficulty not only during the concentration processes but even in the discharge phase of the fermentation broth from the fermenters and transferral to separation or treatment systems for the extraction of lipids.

The Applicant has therefore considered the problem of finding a method for recovering a mucilaginous biomass of oleaginous yeasts from a fermentation broth, through the concentration of the bacterial suspension that comprises said mucilaginous biomass in a sufficiently reduced volume, when the methods and techniques typically used in industrial practice for this purpose prove to be ineffective.

As already mentioned, the high viscosity of the fermentation broth and/or the reduction in the difference in density between the phases of the fermentation broth, can make centrifugation "as such" totally ineffective for recovering oleaginous biomasses from the culture medium.

Among the methods used for the concentration of cell suspensions, filtration on flea membranes or on rotary filters can be mentioned, but the mucilaginous substances produced by the oleaginous microorganisms can rapidly block the pores of said filters thus preventing the permeation of the aqueous phase; resort to spcecific additives (so-called pre-coats or filter aids), on the other hand, besides being of little benefit, can be inadvisable as it negatively interferes with the subsequent extraction treatment of the lipids. These additives are in fact solid materials, for example based on derivatives of cellulose or clays, which, remaining englobed in the biomass, can create problems in the subsequent extraction phase of the lipids (for example causing blockage of the filters, the formation of solid deposits, transfer difficulties by means of pumps, etc.).

Similarly, the addition to the fermentation broth of flocculating agents or sedimentation promoters of the biomass can, in these cases, prove to be ineffective as they are not capable of favouring the separation of the biomass from the liquid phase composed of the fermentation broth. Furthermore, the nature of some flocculating agents can be incompatible with the subsequent extraction processes of lipids, one to the high affinity of these substances with the solvents used in the extraction. In practice, these products could be extracted together with the intracellular lipids and therefore represent impurities to be removed before use of the lipids themselves.

Tangential microfiltration, in particular if equipped with a back-pulse backpressure system, for compensating the reduction in flow-rate due to fouling of the membranes, can be effective for the concentration of the cell suspensions comprising highly mucilaginous biomasses; even this technique, however, does not have a real industrial application as the permeation flow undergoes a sudden drop even after a short time of use, therefore resulting in an unsustainable increase in the treatment times.

Finally, although methods that envisage evaporation of the water contained in the fermentation broth (such as, for example, biomass drum-drying, lyophilization or spray-drying techniques) are effective for concentrating highly mucilaginous cell suspensions, they require a high energy consumption and in any case determine the simultaneous concentration of components present in the fermentation broth that may be incompatible with the subsequent extraction processes or with the use of the lipids extracted.

The Applicant has now found a method for concentrating a cell suspension comprising a mucilaginous biomass of oleaginous yeasts that does not have the drawbacks indicated above.

Said method comprises a heat treatment of the cell suspension of oleaginous yeasts in an acid pH environment, under conditions that do not cause cell lysis, so as to favour the formation of said cell suspension in concentrated form with methods known in the art, for example by means of centrifugation.

Numerous advantages are obtained in applying the method according to the present invention.

Said method, for example, allows the mucilaginous biomass containing intact oleaginous yeast cells to be recovered, i.e. substantially without there being degradation of the cell membranes of said yeasts or cell lysis phenomena, thus avoiding dispersion of the endocellular lipids of interest.

For the purposes of the present invention, the oleaginous yeast cells of a cell suspension are considered intact to the extent in which the lipid content of the fermentation broth removed from the cell suspension at the end of the process according to the method of the present invention, as better described hereunder (Example 5), proves to be substantially null.

Another important advantage lies in the fact that the concentration of the cell suspension effected according to the method of the present invention, allows the removal from the cellular biomass, together with the aqueous phase, of compounds originally present in the fermentation broth or which have been formed as a result of the fermentation, that could harm or reduce the effectiveness of the subsequent lipid extraction treatment.

A further definite advantage of the method lies in the fact that the volume of the cell suspension can be considerably reduced, thus allowing the subsequent lipid extraction treatment to be effected on a reduced scale, with an evident saving in terms of equipment and reagents (for example solvents) and process costs.

For the purposes of the present invention, the concentration of the biomass in the cell suspension is defined as dry weight of the biomass referring to the volume unit of suspension. In particular, "dry weight" of the biomass refers to the weight of the cells contained in a known volume of cell suspension, determined by weighing the above-mentioned cells after eliminating the whole water content by means of heat treatment in a ventilated oven at 105° C. up to a constant weight (about 24 h). Said weight can then be related to 1 liter of cell suspension, and the concentration is therefore expressed in grams/liter (g/L), or it can be related to 100 g of cell suspension, and in this case the concentration of biomass is expressed as percentage with respect to the total weight of the suspension (% "dry weight" or % dw).

Further characteristics and advantages of the present invention will appear evident from the following detailed description and from the non-limiting embodiment examples.

For the purposes of the present description and following claims, the definitions of the numerical ranges always comprise the extremes unless otherwise specified.

For the purposes of the present description and following claims, the percentages refer to weight percentages, unless otherwise specified.

For the purposes of the present description and following claims, the term "comprising" also includes the terms "that essentially consists of" or "that consists of".

For the purposes of the present invention, the term "lipids" refers to a category of substances, generally comprising an aliphatic hydrocarbon chain in the molecule, which dissolve in apolar organic solvents and are poorly soluble in water. Lipids form an essential group of molecules in living cells and comprise, for example, fats, oils, waxes, esters of waxes, sterols, terpenoids, isoprenoids, caroteno polyhydroxy-alkanoates, fatty acids, fatty alcohols, esters of fatty acids, phospholipids, glycolipids, sphingolipids and acylglycerols such as monoglycerides, diglycerides and triglycerides.

For the purposes of the present invention and with particular reference to the cultures of microorganisms and in particular cultures of yeasts, the term "mucilage" refers to a complex of organic substances similar to a gel, capable of withholding liquids, characterized by a viscous and rubbery consistency. Mucilages can consist, for example, of mixtures of polysaccharides, glycolipids, lipopeptides, glycopeptides, polysaccharide-lipid complexes, polysaccharide-protein complexes. In some cases, highly mucilaginous yeast cultures are character by high viscosities, equal to or higher an 15 mPa·s (K. Pavlova, L. Koleva, M. Kratchanova, I. Panchev "Production and characterization of an exopolysaccharide by yeast" (2004), World Journal of Microbiol & Biotechnol., vol 20 pages 435-439).

For the purposes of the present invention, the term "mucilaginous microorganism" refers to a microorganism which, under normal or physiological conditions, or under conditions of metabolic stress, or in the presence of specific substrates and/or under particular fermentation conditions, produces mucilage. The cultivation of mucilaginous microorganisms leads to the production of "mucilaginous biomasses".

For the purposes of the present invention, the term "biodiesel" refers to a fuel for diesel engines comprising alkyl esters (for example methyl, propyl or ethyl esters) of long-chain fatty acids deriving from biological sources.

For the purposes of the present invention, the term "green diesel" refers to a fuel for diesel engines comprising hydrogenation or deoxygenation products of lipids deriving from biological sources in the presence of hydrogen and at least one catalyst.

For the purposes of the present invention, the term "bioplastic" refers to a type of recyclable plastic deriving from renewable raw materials of a biological origin, or it is biodegradable, or has both properties.

For the purposes of the present invention, the term "renewable raw material" refers to a composition at least partially deriving from a source and/or a process which, due to natural features or to the effect of human activity, is considered non-"exhaustible", i.e. it is renewed with time and is therefore almost indefinitely available for exploitation.

For the purposes of the present invention, the expression "oleaginous microorganism" refers to a microorganism capable of accumulating lipids in a quantity equal to or higher than 25% of its cell dry weight. Oleaginous yeasts are included among oleaginous microorganisms.

Some variants of oleaginous yeast can be capable of accumulating lipids in a percentage equal to or higher than 40% with respect to their cell dry weight. Under particular conditions, an oleaginous yeast can accumulate lipids in a percentage preferably equal to or higher than 60% with respect to its cell dry weight.

For the purposes of the present invention, the expressions "cultivation" and "culture" indicate the processes through which the cells of a microorganism grow and reproduce under conditions controlled by human beings. The "fermentation" of oleaginous yeast, effected in some embodiments of the invention, falls within the processes defined by the above-mentioned expressions.

For the purposes of the present invention, the expressions fermentation (or culture) "medium" or "broth", indicate a liquid, or a gel, prepared for sustaining the growth of microorganisms, for example cells of oleaginous yeast.

For the purposes of the present invention, the term "biomass" refers to the combination of cells and/or cell material deriving from plants, animals or microorganisms. In a preferred aspect, biomasses can derive from cells and/or cell material deriving from fungi, bacteria, yeasts, molds and microalgae. Said biomasses can typically be of a natural origin. In some embodiments of the invention, said biomasses can be composed of natural mutants, induced mutants or genetically modified organisms. Said biomasses are preferably produced by fermentation or other culture modes.

An object of the present invention relates to a method for concentrating a cell suspension comprising a mucilaginous biomass of oleaginous yeasts, the above method comprising the following steps:

a) cultivating said oleaginous yeasts in a fermentation broth thus obtaining a cell suspension comprising said mucilaginous biomass;

b) subjecting the cell suspension obtained from step a) to heat treatment, at a temperature within the range of 95° C. to 120° C. and to acid treatment, thus obtaining a treated cell suspension comprising said mucilaginous biomass containing intact oleaginous yeast cells;

c) concentrating the treated cell suspension obtained in step b) comprising a step for removing at least part of said fermentation broth thus obtaining a concentrated cell suspension.

The oleaginous yeasts are preferably selected from the group comprising the genera *Yarrowia, Candida, Cryptococcus, Trichosporon, Trigonopsis, Torulopsis, Lipomyces, Pichia, Rhodotorula, Rhodosporidium,* and consortia thereof, preferably *Trichosporon, Cryptococcus, Rhodosporidium,* or consortia thereof.

The above yeasts preferably accumulate lipids in a quantity equal to or higher than 25%, preferably equal to or higher than 40%, more preferably equal to or higher than 60%, even more preferably equal to or higher than 70% of their dry weight.

In a preferred aspect, said oleaginous yeasts can be represented by cells of the yeast *Rhodosporidium azoricum* DSM 29495.

The mutant strain of oleaginous yeast *Rhodosporidium azoricum* DSM 29495 was obtained with in vitro mutagenesis methods, as described in Italian patent application MI2014A002292 filed by the Applicant, and is characterized by significantly higher intracellular accumulation yields of lipids with respect to the wild-type strain of the same species *Rhodosporidium azoricum* when cultivated in a fermentation broth enriched with nitrogen sources.

The fermentation broths can comprise solutions of sugars obtained from starchy plants or sugary fruits (first-generation sugars). In other embodiments, broths comprising sugars obtained by hydrolytic and saccharification treatment of non-edible lignocellulosic biomasses (second-generation sugars), can be used.

In a preferred aspect of the present invention, the fermentation broth in which the fermentation of oleaginous yeast is effected, can derive from the hydrolysis of lignocellulosic biomasses.

For the purposes of the present invention, the terms "lignocellulosic material" and "lignocellulosic biomass" refer to a complex structure of a vegetable origin comprising cellulose, hemicellulose and lignin. Sugars are obtained from this material, through physico-chemical and enzymatic treatments known in the art, which can be used as carbon sources in fermentation processes of microorganisms for the production of alcohols and/or lipids. In a preferred aspect of the present invention, the sugars obtained from starchy plants or sugary fruits (first-generation sugars) or obtained by hydrolytic and saccharification treatment of non-edible lignocellulosic biomasses (second-generation sugars), are fed to a fermenter in which a pre-culture of oleaginous yeasts is inoculated. In addition to sugars, other nutrients such as vitamins, salts or nitrogenated compounds, can also be fed to the fermenter. The fermentation broth used in the above step a) of the method according to the invention preferably derives from the hydrolysis of lignocellulosic biomasses.

During the above step b) in which the cell suspension is subjected to heat treatment and acidification treatment, the above suspension can be maintained without stirring or it can be subjected to slow, intermittent or continuous stirring. In a preferred aspect, the cell suspension can be kept under slow stirring.

The heat treatment is preferably carried out for a time ranging from 3 to 12 hours, preferably for a time ranging from 4 to 8 hours.

The heat treatment is preferably carried out at a temperature within the range of 100° C. to 110° C. Equivalent treatment can be obtained with different time and temperature combinations. The higher the temperature at which said heat treatment is carried out, for example, the lower the amount of time necessary will be. In particular, in a preferred aspect of the present invention, the heat treatment can be carried out at 100° C. for about 8 hours. In a further preferred aspect of the present invention, the heat treatment can be carried out at 110° C. for about 4 hours.

It should be noted that the above heat treatment differs from other heat treatments and/or pretreatments described in the known art, as said pretreatments, whose purpose is to "pasteurize" biomasses of oleaginous microorganisms and allow preservation for long periods of time before the extraction of the intracellular lipids, are carried out for very reduced times and do not include treatment with acid in the standard protocol. These pasteurization treatments have, in fact, proved to be completely ineffective for concentrating cell suspensions comprising mucilaginous biomasses of oleaginous yeasts.

The method of the present invention, on the contrary, characterized by a synergic effect linked to the acidification treatment combined with the heat treatment for a suitably established time, unexpectedly allows said cell suspensions to be concentrated without any difficulty.

Following the acidification treatment according to the present invention, the pH of the cell suspension can be within the range of 1.5 to 6.0 and preferably within the range of 2.0-4.5.

The acidification treatment can be effected during the heat treatment. In a preferred aspect, the heat treatment is preceded by the above acidification treatment.

The acidification treatment is preferably carried out by the addition of an organic or inorganic Brønsted acid, preferably an inorganic acid.

The acid is preferably selected from the group comprising acetic acid, hydrochloric acid, nitric acid, phosphoric acid, sulfuric acid, boric acid, hydrofluoric acid, hydrobromic acid, lactic acid, formic acid, propionic acid, or mixtures thereof, more preferably sulfuric acid.

It should be noted that the acid used in the method according to the present invention can have any concentration, and it can therefore be an acid diluted in water or a concentrated acid, and is preferably a concentrated acid.

Preferably, the final concentration of said acid, i.e. its concentration in the whole volume of cell suspension at the end of the acidification treatment, can be comprised within the range of 0.05% to 0.5% w/v, and preferably can be comprised within the range of 0.2% to 0.3% w/v.

A skilled person in the field can determine which is the most suitable final concentration of acid, bearing in mind that the pH of the cell suspension, at the end of the addition of said acid, must be within the ranges specified above.

Preferably, the above step c) for concentrating the cell suspension can be effected by means of spontaneous sedimentation or by gravity, siphoning, evaporation under vacuum, lyophilization, flocculation, microfiltration or centrifugation, and said step is even more preferably carried out by centrifugation. In a particularly preferred aspect, step c) can be carried out by discontinuous centrifugation or by continuous centrifugation. In the latter case, a decanter centrifuge with overflow separation or a plate centrifuge, can be used.

When the concentration of cell suspension comprising the mucilaginous biomass of oleaginous yeasts following the heat treatment and acidification treatment according to said method, is carried out by centrifugation, said centrifugation can be effected with an acceleration within the range of 1,000×g to 6,000×g, preferably within the range of 2,000×g to 5,000×g and is even more preferably carried out with an acceleration within the range of 3,000 to 4,000×g.

After centrifugation, the mucilaginous biomass consisting of oleaginous yeasts can form a sediment on the bottom of the centrifugation container or it can be concentrated in a layer that floats on the surface of the culture medium. In this case, the clear infranatant composed of the fermentation broth, can be removed from the floating biomass by means of a suction siphon or by discharging said clear infranatant through a valve suitably positioned in correspondence with the bottom of the container.

It should be noted that the method of the present invention allows a concentrated cell suspension to be obtained, comprising oleaginous yeast cells intact, i.e. without there being any breakage of the yeast cells. It has in fact been shown (Example 5 provided hereunder) that the presence of lipids cannot be found in the fermentation broth removed from the biomass at the end of the process according to said method.

Without wishing to be bound by any particular theory, it is assumed that the method of the present invention favours the degradation of the mucilaginous substances present on the surface of the yeast cells so as to facilitate the aggregation of the same cells and favour the separation from the fermentation broth. By avoiding the destruction of the cell wall, the double advantage is obtained of preventing the dispersion of the intracellular lipids by leakage into the culture medium, and limiting the content of biological and organic material in the aqueous phase which would increase the COD (Chemical Oxygen Demand) index and may require a specific treatment of the exhausted media before being disposed of.

Thanks to the method according to the present invention, after the removal of at least part of the fermentation broth in step c) of said method, the concentration of biomass in the cell suspension obtained can range from 19.0% dw to 35.0% dw, and the concentration preferably ranges from 21.0% dw to 30.0% dw.

After concentrating the cell suspension comprising the biomass of oleaginous yeasts with the process according to the method of the present invention, the above biomass can be subjected to the lysis process and subsequent extraction of the lipids with any of the processes of the known art.

According to the method described in patent application WO2012/052368, for example, the biomass can be transferred to an autoclave where it can be subjected to a further heat treatment at 140° C. for 4 hours, so as to cause its lysis. The suspension obtained can then be transferred to a reactor and subjected to extraction with at least one polar organic solvent immiscible with water (for example ethyl-tert-butyl-ether, methyl-iso-butyl-ketone, ethyl acetate) or at least one apolar organic solvent (for example, iso-octane, hexane, or mixtures of linear or branched paraffins having a number of carbon atoms ranging from 5 to 10, benzene, toluene or xylene) pure or in a mixture with water-soluble polar solvents (for example, ethanol, propanol, isopropanol).

After being extracted in an organic solvent, the mixture of triglycerides contained in the cells can be isolated by evaporation of the organic solvent itself.

The lipid fraction can be analyzed by means of chromatographic techniques, for example by gas chromatography or by High Performance Liquid Chromatography (HPLC) according to processes of the known art.

Through these analytical methods, it has been found that the lipids accumulated in oleaginous yeast cells are represented by at least 90% of triglycerides, preferably glycerol esters of fatty acids having from 8 to 24 carbon atoms, such as, for example, palmitic acid, stearic acid, oleic acid, α-linoleic acid.

Other lipids that can be present are: phospholpids, monoglycerides, diglycerides, free fatty acids, or mixtures thereof.

The lipids obtained according to the process object of the present invention can be advantageously used as synthesis intermediates, particularly in the so-called "green-chemistry" field. They can also be subjected to transesterification in the presence of at least one alcohol having from 1 to 4 carbon atoms, preferably methanol or ethanol, and at least one acid or basic catalyst, in order to produce glycerol and alkyl esters, in particular methyl esters or ethyl esters (biodiesel).

Alternatively, said lipids can be subjected to hydrogenation/deoxygenation in the presence of hydrogen and at least one catalyst in order to produce "green diesel". Hydrogenation/deoxygenation processes are known in the art and are described, for example, in European patent application EP 1 728 844.

Some non-limiting examples are provided for a better illustration of the present invention and for its practical embodiment.

EXAMPLE 1 (FERMENTATION OF THE OLEAGINOUS YEAST *RHODOSPORIDIUM AZORICUM* DSM 29495)

An example is provided hereunder of the preparation of a cell suspension of the oleaginous yeast *Rhodosporidium azoricum* DSM 29495.

200 mL of YEPD medium (yeast extract 10 g/L, peptone 10 g/L, glucose 20 g/L) previously sterilized in an autoclave at 80° C. for 45 minutes, were introduced into a 1 L flask.

The initial fermentation broth thus obtained was inoculated with a sample of the oleaginous yeast strain *Rhodosporidium azoricum* DSM 29495.

This pre-culture was kept at 30° C. under stirring at 200 rpm for 24 hours, and was then transferred to a 20 L fermenter containing 8 L of a medium containing glucose 50 g/L, Corn Steep Solids 5 g/L, yeast extract 2 g/L, $KH_2PO_4$ 6 g/L, $MgSO_4 \cdot 7H_2O$ 0.3 g/L, NaCl 0.06 g/L $CaCl_2 \cdot 2H_2O$ 0.06 g/L, previously sterilized at 80° C. for 45 minutes.

This first culture in the fermenter was maintained at 30° C. for 24 hours, under aerobic conditions by insufflation of 1 L/L·min of sterile air and stirring varying from 600 to 900 rpm, modulated with the air flow so as to maintain the concentration of dissolved oxygen ($DO_2$) equal to 30% of the saturation value.

At the end of 24 hours, the cell suspension obtained was transferred, by means of a peristaltic pump, to a 200 L fermenter, containing 80 L of a medium containing glucose 80 g/L, Corn Steep Solids 8 g/L, yeast extract 3.2 g/L, $KH_2PO_4$ 6 g/L, $MgSO_4 \cdot 7H_2O$ 0.3 g/L, NaCl 0.06 g/L $CaCl_2 \cdot 2H_2O$ 0.06 g/L, $(NH_4)_2SO_4$ 8 g/L previously sterilized at 121° C. for 20 minutes.

This second culture in the fermenter was also maintained at 30° C. for 24 hours, under aerobic conditions by insufflation of sterile air and stirring varying from 600 to 900 rpm, modulated with the air flow so as to maintain the concentration of dissolved oxygen ($DO_2$) equal to 30% of the saturation value, and at a pH equal to about 5.0, maintained by the addition, when necessary, of a few drops of a solution of KOH 5 M or $H_2SO_4$ 10% (vol/vol).

At the end of 24 hours, the content of residual glucose was determined according to processes known in the art, for example using an enzymatic membrane analyzer such as a biochemical analyzer YSI 2900, or by means of ion-exchange chromatography (HPAE-PAD), using a Dionex chromatograph, equipped with a Carbopac PA100 column, with a gradient of sodium hydroxide and sodium acetate as counter-ion.

Two tanks were then connected to the fermenter: a sterile solution of glucose 614 g/L, was introduced into one of these tanks, fed to the fermenter in continuous with an average flow-rate of 1 L/h according to the consumption kinetics of the microorganism in the culture, so as to maintain a constant concentration of glucose in the culture equal to 30 g/L. A sterile solution of yeast extract 80 g/L and $(NH_4)_2SO_4$ 200 g/L, was introduced into the second tank, fed to the fermenter in continuous with an average flow-rate of 400 ml/h.

The fermentation was then continued under the conditions described above for a total of 117 hours.

At the end, the cell suspension (a total of 187 kg) was discharged from the fermenter, and concentration tests were subsequently carried out. The cell suspension thus obtained was characterized by a concentration of the biomass equal to 112.3 g/L of cell dry weight (dw), or 11.23% dw and a total lipid content equal to 51% by weight, with respect to the dry weight of the cells. Furthermore, said suspension was characterized by a viscosity, measured at 30° C. with a Stabinger SVR 3000 Anton Paar microviscometer ("shear rate" 1/1000) equal to 4.1 mPa·s, a density of 1.023 g/cm³ at 30° C., and a mucilaginous appearance.

EXAMPLE 2 ACCORDING TO THE INVENTION (CONCENTRATION TEST OF A CELL SUSPENSION COMPRISING A MUCILAGINOUS BIOMASS OF OLEAGINOUS YEAST *RHODOSPORIDIUM AZORICUM* DSM 29495 BY HEAT TREATMENT AT 100° C. AND ACIDIFICATION TREATMENT)

The present example shows that heat treatment at 100° C. together with an acidification treatment of the cell suspension comprising a mucilaginous biomass of oleaginous yeast is effective for adequately concentrating the same cell suspension.

200 mL of cell suspension obtained according to the process of the previous Example 1, were introduced into a 500 mL autoclave and 0.4 g of $H_2SO_4$ 96% (corresponding to a concentration of acid equal to 0.2% by weight with respect to the volume of the same suspension) were added. The pH obtained was equal to 3.2. The cell suspension was then brought to 100° C. and kept at this temperature for 8 hours under slow stirring. At the end, after cooling, the separation of a clear infranatant and an upper phase consisting of the cell biomass separated, was observed.

After cooling, the cell suspension was then discharged from the autoclave and introduced into centrifugation containers and centrifuged at 3,000×g for 10 minutes at 20° C. with a Thermo-Scientific IEC-CL31R Multispeed centrifuge.

At the end of the centrifugation, the cell suspension comprising cells rich in lipids was concentrated in an upper "floating" phase above a clear infranatant composed of the fermentation broth. After removing the clear infranatant, 85.73 mL of concentrated cell suspension were obtained, characterized by a concentration of biomass equal to 26.2% dw, adequate for the purposes of the subsequent lipid extraction process.

EXAMPLE 3 ACCORDING TO THE INVENTION (CONCENTRATION TEST OF A CELL SUSPENSION COMPRISING A MUCILAGINOUS BIOMASS OF OLEAGINOUS YEAST *RHODOSPORIDIUM AZORICUM* DSM 29495 BY HEAT TREATMENT AT 110° C. AND ACIDIFICATION TREATMENT)

The present example shows that heat treatment at 110° C. together with an acidification treatment of the cell suspension comprising a mucilaginous biomass of oleaginous yeast is also effective for adequately concentrating the same cell suspension.

200 mL of cell suspension obtained according to the process of the previous Example 1, were introduced into a 500 mL autoclave and 0.4 g of $H_2SO_4$ 96% (corresponding to a concentration of acid equal to 0.2% by weight with respect to the volume of the suspension) were added. The pH obtained was equal to 3.2. The cell suspension was then brought to 110° C. and kept at this temperature for 4 hours under slow stirring. After cooling, the cell suspension was then discharged from the autoclave and introduced into centrifugation containers and centrifuged at 3,000×g for 10 minutes at 20° C. with a Thermo-Scientific IEC-CL31R Multispeed centrifuge.

At the end of the centrifugation, the cell suspension comprising cells rich in lipids was concentrated in an upper "floating" phase above a clear infranatant composed of the fermentation broth. After removing the clear infranatant, 80 mL of concentrated cell suspension were obtained, characterized by a concentration of biomass equal to 28.1% dw, adequate for the purposes of the subsequent lipid extraction process.

EXAMPLE 4 ACCORDING TO THE INVENTION (CONCENTRATION OF A CELL SUSPENSION COMPRISING A MUCILAGINOUS BIOMASS OF OLEAGINOUS YEAST *RHODOSPORIDIUM AZORICUM* DSM 29495 BY HEAT TREATMENT AT 110° C. AND ACIDIFICATION TREATMENT)

The present example shows that heat treatment at 110° C. together with an acidification treatment of the cell suspension comprising a mucilaginous biomass of oleaginous yeast, effected according to the previous Example 3, is effective for adequately concentrating said cell suspension even when applied on a large scale.

14.4 kg of cell suspension obtained according to the process of the previous Example 1, were introduced into a 20 L autoclave and 28.8 g of $H_2SO_4$ 96% (corresponding to a concentration of acid equal to 0.2% by weight with respect to the volume of the same cell suspension) were added. The pH obtained was equal to 3.2. The cell suspension was then brought to 110° C. and kept at this temperature for 4 hours under slow stirring. At the end, after cooling, the entire cell suspension was then discharged from the autoclave and introduced into centrifugation containers and centrifuged at 3,000×g for 10 minutes at 20° C. with a Beckman Coulter Avanti J-26XP centrifuge with a fixed-angle rotor JLA-8.1000.

After centrifugation, the cell suspension comprising cells rich in lipids was concentrated in an upper "floating" phase above a clear infranatant composed of the fermentation broth. After removing the clear infranatant, 7.7 kg of concentrated cell suspension were obtained, characterized by a concentration of biomass equal to 21.2% dw, adequate for the purposes of the subsequent lipid extraction process.

EXAMPLE 5 (DETERMINATION OF THE LIPID CONTENT OF THE INFRANATANT OBTAINED AFTER HEAT TREATMENT AT 110° C. AND ACIDIFICATION TREATMENT)

The present example shows that heat treatment together with acidification treatment allows a cell suspension to be obtained, in which the oleaginous yeast cells are intact, or in other words, it does not cause lysis of the oleaginous cells.

500 mL of clear centrifugation infranatant obtained according to the process of the previous Example 4 were introduced into a jacketed glass reactor, equipped with a stirrer and condenser. 1 L of pure iso-octane (99.8%) were added to said infranatant, the temperature was brought to 80° C. under stirring so as to have a perfect mixing of the two immiscible liquid phases. The suspension was maintained under these temperature and stirring conditions for 2 hours, and was then left to cool to room temperature without stirring, in order to favour the separation of the underlying aqueous phase from the upper organic phase, which was removed and collected in a distillation flask, from which the solvent was then evaporated under vacuum. Analysis of the residue after evaporation of the solvent confirmed that no lipids were contained therein.

EXAMPLE 6 (COMPARATIVE) (CONCENTRATION TEST OF A CELL SUSPENSION COMPRISING A MUCILAGINOUS BIOMASS OF OLEAGINOUS YEAST *RHODOSPORIDIUM AZORICUM* DSM 29495 BY MEANS OF CENTRIFUGATION)

The concentration method of a cell suspension according to the present invention was compared with the techniques used as usual practice for recovering the biomass after fermentation, by means of some tests on samples of cell suspension obtained with the process of Example 1.

The present example shows that centrifugation is not effective for adequately concentrating the cell suspension comprising a mucilaginous biomass of oleaginous yeast, unless it is preceded by the treatment according to the method of the present invention.

14 mL of cell suspension obtained as described in Example 1, were introduced into a graded centrifuge test-tube and subjected to centrifugation in a Thermo-Scientific IEC-CL31R Multispeed centrifuge at 3,000×g for 5 minutes at 20° C. At the end of the centrifugation, the separation of 2 ml of clear infranatant was observed, whereas the remaining volume (12 mL, equal to 85.7% vol/vol) remains turbid. The cell suspension was then concentrated 1.16 times, reaching a concentration of the biomass equal to 13.1% dw. This value is not adequate for the purposes of the subsequent lipid extraction process.

EXAMPLE 7 (COMPARATIVE) (CONCENTRATION TEST OF A CELL SUSPENSION COMPRISING A MUCILAGINOUS BIOMASS OF OLEAGINOUS YEAST *RHODOSPORIDIUM AZORICUM* DSM 29495 BY MEANS OF HEAT TREATMENT AND CENTRIFUGATION)

The present example shows that simple heat treatment of the fermentation broth before centrifugation is not effective, alone, for adequately concentrating the suspension comprising a mucilaginous biomass of oleaginous yeast.

200 mL of cell suspension obtained as described in Example 1, were introduced into a 500 mL autoclave and brought to 110° C. for 4 hours under slow stirring.

At the end, 14 mL of cell suspension subjected to heat treatment were introduced into a graded centrifuge test-tube and subjected to centrifugation in a Thermo-Scientific IEC-CL31R Multispeed centrifuge at 3,000×g for 5 minutes at 20° C. At the end of the centrifugation, the separation of 0.5 ml of clear infranatant was observed, whereas the remaining volume (13.5 mL, equal to 96.4% vol/vol) remains turbid. The cell suspension was then concentrated only 1.04 times, reaching a concentration of the biomass equal to 11.6% dw. This value is not adequate for the purposes of the subsequent lipid extraction process.

EXAMPLE 8 (COMPARATIVE) (CONCENTRATION TEST OF A CELL SUSPENSION COMPRISING A MUCILAGINOUS BIOMASS OF OLEAGINOUS YEAST *RHODOSPORIDIUM AZORICUM* DSM 29495 BY THE ADDITION OF ACID AND CENTRIFUGATION)

The present example shows that simple treatment with acid without heat treatment of the cell suspension before centrifugation is not effective, alone, for adequately concentrating the cell suspension itself.

200 mL of cell suspension obtained as described in Example 1, were introduced into a 500 mL flask and 0.4 g of $H_2SO_4$ 96% (corresponding to a concentration of acid equal to 0.2% by weight with respect to the volume of the cell suspension) were added. The pH obtained is equal to 3.2. The flask is then placed in an orbital shaker (MPM Instruments) with temperature set at 30° C. and kept under slow stirring for 8 hours.

At the end, 14 mL of cell suspension subjected to treatment were introduced into a graded centrifuge test-tube and subjected to centrifugation in a Thermo-Scientific IEC-CL31R Multispeed centrifuge at 3,000×g for 5 minutes at 20° C. At the end of the centrifugation, no phase separation was observed, showing that the treatment effected is not adequate for obtaining a concentration of the cell suspension at the desired level.

EXAMPLE 9 (COMPARATIVE) (CONCENTRATION TEST OF A CELL SUSPENSION COMPRISING A MUCILAGINOUS BIOMASS OF OLEAGINOUS YEAST *RHODOSPORIDIUM AZORICUM* DSM 29495 BY MEANS OF TANGENTIAL MICROFILTRATION)

The present example shows that tangential microfiltration, like centrifugation, is not effective for adequately concentrating the cell suspension comprising a mucilaginous biomass of oleaginous yeast, unless preceded by the treatment according to the method of the present invention.

93.6 kg of cell suspension obtained as described in Example 1 were subjected to tangential microfiltration using the plant Hydro Air HAR P19 in "back pulse" mode and 0.2 µm ceramic membranes.

The microfiltration was carried out for 6 hours at room temperature at a flow-rate value equal to 8,000 L/h, producing 40.5 kg of retentate (concentrated cell suspension) and 53.1 kg of permeate (cell-free fermentation broth). The concentrated cell suspension is characterized by a concentration of biomass equal to 195 g/L (i.e. 19.5% dw). This value proves to be barely adequate for the purposes of the subsequent lipid extraction process.

During the microfiltration, however, the permeation flow dropped from the initial 60 kg·h$^{-1}$·m$^{-2}$ to about 10 kg·h$^{-1}$·m$^{-2}$. Said final permeation flow is too low for being conveniently applied to an industrial process.

The cell suspension used, comprising a mucilaginous biomass of Rhodosporidium azoricum DSM 29495, apparently caused a deterioration in the performances of the filter membrane used in the microfiltration process. Even if, in fact, at the end of the microfiltration process, the membranes were regenerated according to the instructions of the producer by washing them with 150 L of distilled water for about 5 hours, followed by 60 L of a solution of NaOH 0.5% by weight for a further 5 hours and finally with a further 150 L of distilled water for a further 5 hours, the permeation flows were not restored to the characteristic values of the membrane.

In conclusion, even if tangential microfiltration is effective for concentrating the cell suspension comprising a mucilaginous biomass of oleaginous yeast, this technique practically cannot be applied to the industrial process due to the degradation in the performances of the device after a single treatment.

EXAMPLE 10 (COMPARATIVE)
(CONCENTRATION TEST OF A CELL
SUSPENSION COMPRISING A
MUCILAGINOUS BIOMASS OF OLEAGINOUS
YEAST RHODOPORIDIUM AZORICUM DSM
29495 BY MEANS OF FLOCCULATION)

The present example shows that flocculation, like centrifugation and tangential microfiltration, is not effective for adequately concentrating the cell suspension comprising a mucilaginous biomass of oleaginous yeast, unless preceded by the treatment according to the method of the present invention.

200 mL of cell suspension obtained as described in Example 1, were introduced into a 500 mL graded cylinder, and a cationic flocculating suspension based on polyacrylamide (Basf Zetag® 9068FS) was added, very slowly and under bland stirring to said suspension, at room temperature (20° C.); the onset of flocculation was observed after the addition of 0.5 g of flocculating agent, corresponding to a dosage equal to about 2.5 kg/m$^3$ of suspension. This quantity is considered excessive for application in industrial processes, above all due to the fact that in any case the effectiveness of the treatment is not satisfactory. At the end of the addition of the flocculating agent, in fact, only 50 ml of clear fermentation broth were separated, with a consequent concentration of biomass in the cell suspension from the initial 11.3% dw to 15.0% dw. This value is not adequate for the purposes of the subsequent lipid extraction process.

EXAMPLE 11 (EXTRACTION OF LIPIDS FROM
THE CONCENTRATED CELL SUSPENSION
COMPRISING A MUCILAGINOUS BIOMASS
OF OLEAGINOUS YEAST)

The present example shows that the concentrated cell suspension obtained with the method according to the present invention can be advantageously subjected to an extraction process of intracellular lipids.

5.9 kg of concentrated cell suspension obtained in accordance with the previous Example 4, and corresponding to 1.25 kg of cell dry weight, were introduced into a 20 L autoclave, brought to 140° C. and kept at this temperature for 4 hours.

At the end of the treatment, the suspension obtained was transferred to a 30 L jacketed glass reactor equipped with a stirrer and condenser. 3 L (equal to 2,073 g) of pure iso-octane (99.8%) were added to the suspension, the temperature was brought to 80° C. under stirring so as to guarantee a perfect mixing of the two immiscible phases. The mixture was maintained under these temperature and stirring conditions for 2 hours, and was then left to cool to room temperature (20° C.) without stirring, in order to favour the separation of the underlying aqueous phase from the upper organic phase, which was removed and collected in an appropriate container.

The extraction process with iso-octane at 80° C. for hours under stirring was repeated a further two times, using the same quantity of fresh iso-octane for each cycle. The organic phases of the three extraction processes were joined in the same container and were subsequently subjected to evaporation of the solvent. The residue obtained after removing the solvent was weighed and analyzed, providing a lipid content which amounted to 620.3 g, corresponding to an extraction yield equal to 98% by weight with respect to the total theoretical quantity.

EXAMPLE 12 (FERMENTATION OF THE
OLEAGINOUS YEAST CRYPTOCOCCUS
CURVATUS ATCC 20509)

An example is provided hereunder for the preparation of a cell suspension comprising a mucilaginous biomass of oleaginous yeast Cryptococcus curvatus ATCC 20509.

200 mL of YEPD medium (yeast extract 10 g/L, peptone 10 g/L, glucose 20 g/L) previously sterilized in an autoclave at 80° C. for 45 minutes were introduced into a 1 L flask.

The initial fermentation broth thus obtained was inoculated with a sample of the oleaginous yeast strain Cryptococcus curvatus ATCC 20509.

The culture was kept at 30° C. under stirring at 200 rpm for 24 hours, and was then transferred to a 20 L fermenter containing 6 L of a medium containing glucose 100 g/L, Corn Steep Solids 5 g/L, yeast extract 2 g/L, $(NH_4)_2SO_4$ 5 g/L, $KH_2PO_4$ 6 g/L, $MgSO_4.7H_2O$ 0.3 g/L, NaCl 0.06 g/L $CaCl_2.2H_2O$ 0.06 g/L, previously sterilized at 80° C. for 45 minutes.

This culture in the fermenter was kept at 30° C. for 24 hours, under aerobic conditions by insufflation of 1 L/L·min of sterile air and stirring varying from 600 to 900 rpm, modulated with the air flow so as to maintain the concentration of dissolved oxygen ($DO_2$) higher than 30% of the saturation value, and at a pH of about 5.0, maintained by the addition, when necessary, of a few drops of a solution of KOH 5 M or $H_2SO_4$ 10% (vol/vol).

At the end of 24 hours, 32.5 g of $(NH_4)_2SO_4$ and 200 mL of Corn Steep Liquor, were added to the broth in the fermenter, a tank was then connected to the fermenter, containing a sterile solution of glucose 600 g/L fed in continuous to the fermenter with a variable flow-rate ranging from 50 to 100 mL/h, according to the consumption kinetics of the microorganism in the culture, so as to maintain a constant concentration of glucose in the culture equal to 30 g/L.

The fermentation was then continued under the conditions described above for a total of 140 hours.

At the end, a total of 8.6 L of cell suspension were discharged from the fermenter, characterized by a concentration of the biomass equal to 118 g/L dry weight, or 11.8% dw and by a total lipid content equal to 66% by weight, with respect to the dry weight of the cells. Furthermore, said cell suspension was characterized by a viscosity, measured at 30° C. with a Stabinger SVR 3000 Anton Paar microviscometer ("shear rate" 1/1000) equal to 160 mPa·s.

EXAMPLE 13 ACCORDING TO THE INVENTION (CONCENTRATION OF A CELL SUSPENSION COMPRISING A MUCILAGINOUS BIOMASS OF OLEAGINOUS YEAST *CRYPTOCOCCUS CURVATUS* ATCC 20509 BY HEAT TREATMENT AT 110° C. AND ACIDIFICATION TREATMENT)

The present example shows that heat treatment at 110° C. together with an acidification treatment according to the present invention, is also effective for adequately concentrating a cell suspension comprising a mucilaginous biomass of oleaginous yeast *Cryptococcus curvatus* ATCC 20509.

200 mL of cell suspension obtained according to the process of the previous Example 12, were introduced into a 500 mL autoclave and 0.4 g of $H_2SO_4$ 96% (corresponding to a concentration of acid equal to 0.2% by weight with respect to the volume of the cell suspension) were added. The pH obtained was equal to 3. The cell suspension was then brought to 110° C. and kept at this temperature for 4 hours. At the end, after cooling, the viscosity of the suspension treated was measured with a Stabinger SVR 3000 Anton Paar microviscometer ("shear rate" 1/1000) at 30° C., providing a viscosity value equal to 18 mPa·s.

The cell suspension was then discharged from the autoclave and introduced into centrifugation containers and centrifuged at 3,000×g for 10 minutes at 20° C. with a Beckman Coulter Avanti J-26XP centrifuge with a fixed-angle rotor JLA-8.1000.

At the end of the centrifugation and removal of the clear infranatant, 80 mL of concentrated cell suspension were obtained, characterized by a concentration of biomass equal to 29.5% dw, adequate for the purposes of the subsequent lipid extraction process.

A determination of the lipid content was carried out on the clear infranatant as described in the previous Example 5. Also in this case, the analysis of the residue obtained showed that no lipids are contained in the same, confirming that the concentration method according to the invention allows a cell suspension to be obtained, in which the oleaginous yeast cells are intact, i.e., in other words, said method does not determine lysis of the cells.

The invention claimed is:

1. A method for concentrating a cell suspension comprising a mucilaginous biomass of at least one oleaginous yeast, the method comprising:
   a) subjecting the at least one oleaginous yeast to fermentation in a fermentation broth to obtain a cell suspension comprising the mucilaginous biomass;
   b) after the fermentation, directly subjecting the cell suspension obtained from a) to heat treatment at a temperature of from 95° C. to 120° C. and to acid treatment, thereby obtaining a treated cell suspension comprising the mucilaginous biomass comprising intact oleaginous yeast cells; and
   c) concentrating the treated cell suspension obtained in b), comprising removing at least a part of the fermentation broth, thereby obtaining a concentrated cell suspension.

2. The method according to claim 1, wherein in the b), the heat treatment is preceded by the acid treatment.

3. The method according to claim 1, wherein the at least one oleaginous yeast is selected from the group consisting of the genera *Yarrowia, Candida, Cryptococcus, Trichosporon, Trigonopsis, Torulopsis, Lipomyces, Pichia, Rhodotorula, Rhodosporidium*, and a combination thereof.

4. The method according to claim 1, wherein the yeast cells in the obtained concentrated cell suspension comprise 25% or higher, of their dry weight, of lipids.

5. The method according to claim 1, wherein the fermentation broth is derived from hydrolysis of lignocellulosic biomasses.

6. The method according to claim 1, wherein the heat treatment is carried out at a temperature of from 100° C. to 110° C.

7. The method according to claim 1, wherein the heat treatment is carried out for 3 to 12 hours.

8. The method according to claim 1, wherein following the acid treatment, a pH of the cell suspension is from 1.5 to 6.0.

9. The method according to claim 1, wherein the acid treatment is carried out by adding an organic or an inorganic Brønsted acid.

10. The method according to claim 9, wherein the acid is at least one selected from the group consisting of acetic acid, hydrochloric acid, nitric acid, phosphoric acid, sulfuric acid, boric acid, hydrofluoric acid, hydrobromic acid, lactic acid, formic acid, and propionic acid.

11. The method according to claim 1, wherein in the c) concentrating of the cell suspension is carried out by spontaneous sedimentation or gravity, siphoning, vacuum evaporation, lyophilization, flocculation, microfiltration or centrifugation.

12. The method according to claim 1, wherein after the removing of the at least a part of the fermentation broth in the c) a biomass concentration in the obtained cell suspension is from 19.0% dw to 35.0% dw.

13. A method for concentrating a cell suspension comprising a mucilaginous biomass of at least one oleaginous yeast, the method comprising:
   a) subjecting the at least one oleaginous yeast to fermentation in a fermentation broth to obtain a cell suspension comprising the mucilaginous biomass;
   b) after the fermentation, directly subjecting the cell suspension obtained from a) to heat treatment at a temperature of from 95° C. to 120° C. and to acid treatment, thereby obtaining a treated cell suspension comprising the mucilaginous biomass comprising intact oleaginous yeast cells without degradation of a cell membrane of the oleaginous yeast cells and cell lysis, wherein the fermentation broth in the treated cell suspension does not contain endocellular lipids; and
   c) concentrating the treated cell suspension obtained in b), comprising removing at least a part of the fermentation broth, thereby obtaining a concentrated cell suspension comprising the mucilaginous biomass comprising intact oleaginous yeast cells, wherein the removed fermentation broth does not contain endocellular lipids.

* * * * *